United States Patent
Wolf et al.

(10) Patent No.: US 11,612,680 B2
(45) Date of Patent: Mar. 28, 2023

(54) PERITONEAL DIALYSIS MACHINE

(71) Applicant: FRESENIUS MEDICAL CARE DEUTSCHLAND GMBH, Bad Homburg (DE)

(72) Inventors: Klaus Wolf, Arnstein-Muedesheim (DE); Sebastian Hoelzle, Frankfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 992 days.

(21) Appl. No.: 15/752,104

(22) PCT Filed: Aug. 10, 2016

(86) PCT No.: PCT/EP2016/001383
§ 371 (c)(1),
(2) Date: Feb. 12, 2018

(87) PCT Pub. No.: WO2017/025200
PCT Pub. Date: Feb. 16, 2017

(65) Prior Publication Data
US 2018/0236157 A1   Aug. 23, 2018

(30) Foreign Application Priority Data
Aug. 11, 2015   (DE) .................... 10 2015 010 467.5

(51) Int. Cl.
*A61M 1/28*   (2006.01)
(52) U.S. Cl.
CPC .............. *A61M 1/282* (2014.02); *A61M 1/28* (2013.01); *A61M 2205/3334* (2013.01); *A61M 2205/3368* (2013.01); *A61M 2205/3393* (2013.01); *A61M 2205/36* (2013.01); *A61M 2209/084* (2013.01)

(58) Field of Classification Search
CPC ........ A61M 1/28; A61M 1/281; A61M 1/282; A61M 1/284; A61M 1/285; A61M 1/287; A61M 1/288
See application file for complete search history.

(56) References Cited

U.S. PATENT DOCUMENTS

| | | | |
|---|---|---|---|
| 5,141,492 A * | 8/1992 | Dadson | A61M 1/28 604/28 |
| 5,782,796 A * | 7/1998 | Din | A61M 1/28 604/27 |
| 2007/0276328 A1* | 11/2007 | Childers | A61M 1/1643 604/131 |

(Continued)

FOREIGN PATENT DOCUMENTS

| | | |
|---|---|---|
| CA | 2223846 | 6/1999 |
| EP | 0028371 | 5/1981 |

(Continued)

*Primary Examiner* — Dung T Ulsh
(74) *Attorney, Agent, or Firm* — Jacobson Holman PLLC

(57) ABSTRACT

A peritoneal dialysis machine having a machine housing and having a heating receiver as well as having a plurality of solution bags is provided.
The peritoneal dialysis machine furthermore has a hose set which is connected to the solution bags, wherein the plurality of solution bags are arranged in the heating pan and wherein the hose set does not have any heating bag into which the liquid draining from the solution bags runs.

20 Claims, 12 Drawing Sheets

(56) References Cited

U.S. PATENT DOCUMENTS

| | | | |
|---|---|---|---|
| 2007/0287966 A1* | 12/2007 | Keeley | A61M 1/167 604/246 |
| 2009/0009179 A1* | 1/2009 | Sobue | A61M 1/1668 324/519 |
| 2009/0187138 A1* | 7/2009 | Lundtveit | A61M 1/1668 604/29 |
| 2009/0299273 A1* | 12/2009 | Lee | A61M 1/166 604/29 |
| 2009/0312694 A1 | 12/2009 | Bedingfield et al. | |

FOREIGN PATENT DOCUMENTS

| | | |
|---|---|---|
| FR | 2762991 | 11/1998 |
| WO | WO 95/20985 | 8/1995 |
| WO | WO 2010/096657 | 8/2010 |

* cited by examiner

STAND DER TECHNIK

PERITONEAL DIALYSIS MACHINE

BACKGROUND OF THE INVENTION

1. Field of the Invention

The present invention relates to a peritoneal dialysis machine having at least one machine housing and having at least one heating pan as well as having a plurality of solution bags, wherein the peritoneal dialysis machine furthermore has at least one hose set which is connected to the solution bags. The machine in accordance with the invention is preferably a gravimetrically working peritoneal dialysis machine which conveys dialyzate from and to the patient without the use of pumps.

2. Description of the Related Art

Peritoneal dialysis machines known from the prior art have a machine housing and a IV pole which is located above the machine housing and at which a plurality of solution bags are hung which contain dialysis solution to be administered to the patient. A heating pan is furthermore provided in which a heating bag is located. The dialysis solution is transferred into the heating bag from the solution bags and is subsequently administered to the patient.

A schematic setup of such a known machine can be seen from FIG. 12.

The solution bags are marked by the reference numeral 100 in FIG. 12. Reference numeral 110 marks the heating bag which is on the weighing and heating plate 200 of the peritoneal dialysis machine.

The fresh dialyzate introduced into the heating bag 110 is weighed and is set to the correct temperature and is subsequently supplied to the patient P. The measurement of the temperature of the dialyzate takes place using the temperature sensor T. The valves V2 and V3, which are arranged at the machine side and which cooperate with the line section L1, are located between the solution bags 100 and the heating bag 110. The inlet valve V1, which is arranged at the machine side and which controls the fluid flow from the heating bag 110 to the patient P, cooperates with the line section L2 from the heating bag 110 to the patient P.

If the consumed dialyzate is led off from the patient by means of the line section L3, it first moves into the weighing bag 120. The weighing bag is connected to a weighing cell 210 which determines the weight of the weighing bag 120. The outlet valve V4 arranged at the machine side cooperates with the line section L3.

After the weighing of the consumed dialyzate by the weighing cell 210, the dialyzate moves through the line section into the waste bag 130 with which the consumed dialyzate is discarded. The drainage valve V5, which is arranged at the machine side and which is arranged in parallel with the outlet valve V4, cooperates with the line section L4.

The line sections L1 to L4 form the hose set.

It is disadvantageous with this machine known from the prior art that a large height (approximately 1.7 m) has to be overcome for positioning the solution bags and the loading of the machine is thus made correspondingly more difficult. Apart from this, the stability is limited due to the comparatively high center of gravity of the machine due to the stocking of the bags (as a rule 10 l (2×5 l) or 30 l (5×6 l) as well as due to the bag located on the heating pan 110.

Due to the large distance between the solution bags and the heating pan, correspondingly long hose lines of the hose set are furthermore required.

SUMMARY OF THE INVENTION

It is the underlying object of the present invention to further develop a peritoneal dialysis machine of the initially named kind such that it has a compact design.

This object is achieved by a peritoneal dialysis machine in which provision is made such that the plurality of solution bags are arranged in the at least one heating pan and the hose set is not connected to any heating bag into which the liquid draining from the solution bags runs. Differing from the arrangement known from the prior art, at least one solution bag, preferably all solutions bags, containing the fresh dialyzate or a liquid for preparing the dialyzate, is/are not located at an IV pole, but in the heating pan of the machine, and no heating bag is present. The solution bags are therefore not first hung on an IV stand or on the IV pole which extends upwardly starting from the machine housing. Instead, the solution bags are placed together in one or more heating pans. An IV pole is thus preferably not present.

Nevertheless, an embodiment is also covered by the invention which has an IV pole at which one or more solution bags are located.

The heating pan is preferably located above the machine housing of the peritoneal dialysis machine in which the machine control and the display elements and/or operating elements are located. The heating pan can be directly connected to the machine housing.

The heating pan has a size such that, where possible, all the solution bags required for a treatment can be received therein. However, the case is also covered by the invention that not all the solution bags required for a treatment are located in the heating pan, but rather only some of them.

It is conceivable that the solution bags are arranged next to one another and/or above one another, i.e. stacked, in the heating pan. A thermal balance is established by the direct contact of the solution bags stacked above one another and solution bags arranged further away from the heating plate are also sufficiently heated due to this thermal balance.

It is preferred for the solution bags to be arranged next to one another in the heating pan.

The advantage of the arrangement of the solution bags in accordance with the invention comprises a smaller construction height of the overall machine since, in a preferred embodiment of the invention, an IV pole can be dispensed with and the solution bags are arranged close to the machine housing.

A further advantage comprises a simplified handling since the solution bags only have to be placed into the heating pan which is preferably located at a lower height than the hang-in positions of an IV pole with known machines. The further advantage results from this that the hose lines can be reduced in length.

A preferred length of the hose set lies in the range from 3 m to 4.5 m, preferably in the range from 3.5 m to 4.0 m.

A further advantage comprises the fact that no separate heating bag is required into which solution originating from the solution bag or the dialyzate runs. The omission is made possible in that the solutions bags and thus the dialyzate itself located therein are heated.

The hose set from the solution bags to the patient thus has no heating bag and is simplified for this reason and due to the smaller hose length required.

The present invention furthermore relates to a peritoneal dialysis machine having at least one weighing device at which at least one receiving bag is arranged for receiving the draining dialyzer and having at least one hose set which is connected to the receiving bag or bags, wherein the at least one receiving bag is not connected to a waste bag in which the run-off dialyzate is collected, but rather itself forms the waste bag and the weighing bag, i.e. the bag weighed using the weighing device.

Known gravimetric peritoneal dialysis machines have a separate weighing bag for balancing, said bag being marked by reference numeral 120 in FIG. 12. With known peritoneal dialysis machines, the consumed dialyzate, i.e. the drainage fluid, is then let out into a drain container (reference numeral 130 in FIG. 12).

In accordance with another aspect of the invention, a separate weighing bag is dispensed with since the draining consumed dialyzate is let off directly into a drain container, i.e. into the drainage bag. A corresponding simplification of the hose set on the drainage side results from this. In accordance with this aspect of the invention, no bag (weighing bag) is thus provided which only has the object of weighing the consumed dialyzate and from which the dialyzate is conducted into a waste bag. The drainage bag rather serves as a weighing bag and simultaneously also forms the waste bag. A further waste bag into which the consumed dialyzate is transferred is not provided.

A combination of the two ideas in accordance with the present invention, namely that the plurality of solution bags are arranged in the heating pan, with no heating bag being present into which the liquid draining from the solution bag runs, and the receiving bag is not in fluid communication with a waste bag in which the drained dialyzate is collected but rather the receiving bag itself forms the waste bag, is also conceivable and is also covered by the present invention.

As stated above, it is advantageous for the peritoneal dialysis machine not to have any IV pole to which solution bags are fastened. All the solution bags which contain the fresh dialyzate are preferably received in the heating pan.

An embodiment is nevertheless also covered by the invention in which one or more IV poles are provided.

In a preferred embodiment of the invention, the peritoneal dialysis machine has at least one machine housing, wherein the heating pan is arranged above the machine housing and is preferably directly connected to the machine housing.

If all the solution bags required for a treatment are received in the heating pan, the latter has to have a corresponding size.

It is conceivable that the solution bags are arranged above one another and/or preferably next to one another in the heating pan. The advantage results on an arrangement of the solution bags above one another that solution bags not contacting the heating pan directly are also heated due to a thermal balance which is adopted.

The at least one hose set can be configured such that it is simultaneously in fluid communication with two or more than two solution bags so that a mixed solution can be prepared. At least two, preferably three, solution bags can be connected simultaneously due to the arrangement of a plurality of, and preferably all solution bags required for a treatment in or on the heating pan and can e.g. be connected via a Y piece to the feed hose to the patient connector of the patient line. A further shortening of the hose can thereby be achieved.

The connected solution bags are preferably arranged next to one another to achieve a uniform emptying of the solution bags.

If the connected solution bags have different concentrations, a desired mixing ratio can be set in the solution administered to the patient with a simultaneous removal of the dialyzate from the solution bags.

Due to the arrangement of the solution bags, preferably not only the heating bag can be dispensed with, but also the associated valve for the flow control from the heating bag to the patient, with the valve being marked by the reference symbol V1 in FIG. 12.

The hose set preferably only cooperates with exactly one valve (fluid control valve) in the region between a solution bag and the end of the hose set to which the patient port is connected. Only one valve is thus associated with the plurality of solution bags, with the exception of the last bag. With an open valve, dialyzate runs out of the respective solution bag to the patient; the inflow is suppressed with a closed valve. In addition, a valve can be provided for the so-called "last bag", with the valve controlling the inflow of the solution located therein to the patient.

Apart from a simplification of the hose set, there is also an improved balancing due to the omission of the heating bag since there is no running of dialyzate from the heating bag and since also no residual liquid remains in the heating bag.

The weighing device preferably has at least one weighing pan, with the receiving bag or bags being arranged in the weighing pan.

Due to the omission of a weighing bag, the associated valve, which is marked by the reference symbol V5 in FIG. 12, can also be dispensed with.

Provision is preferably made that only exactly one valve (drainage valve) is provided in the hose set between the end of the hose set to which it is connected to a patient port and the receiving bag. If it is open, consumed dialyzate runs into the receiving bag; if it is closed, the valve prevents a drainage of dialyzate from the patient.

The receiving bag or bags is preferably received in the weighing pan and preferably lies in it.

The weighing pan can be connected to a weighing cell of the peritoneal dialysis machine via at least one holding apparatus. The holding apparatus preferably extends in the vertical direction. This embodiment brings about the advantage that the weighing pan, and thus also the receiving bag, i.e. the drainage bag, can be arranged in direct proximity to the floor so that the gravimetric range can be well utilized or there is a sufficient height difference between the patient and the receiving bag. In known machines, a weighing bag is arranged beneath the machine housing, but not close to the floor so that a correspondingly smaller height difference results.

It is preferred for the weighing pan to be arranged at a height of <20 cm, preferably <10 cm, above the floor on which the peritoneal dialysis machine stands.

An ideal flow rate can be achieved due to the achieved increased spacing between the heating pan and the drain pan or weighing pan, i.e. the pan in which the at least one receiving bag is located.

If a level of the patient of approx. 50 to 60 cm above the floor is assumed, the inflow speed for the fresh dialyzate corresponds to the outflow speed of the consumed dialyzate when the spacing between the heating pan and the drainage bag amounts to approximately 1 m±20 cm and the receiving bag or the pan receiving it is located just above the floor.

If the receiving bag has a flat shape, a constant outflow speed can furthermore be realized independently of the degree of filling of the receiving bag.

It is conceivable that the weighing cell is arranged in or at the machine housing and/or in that the holding apparatus comprises a film or another flexible material in which the pan is placed or in that the holding apparatus comprises a rod which is preferably located on the rear side of the machine housing remote from the front side of the machine housing.

The weighing pan, i.e. the pan in which the receiving bag or bags is/are located, can be held e.g. via a film, e.g. a transparent film, guided at both sides. A mechanical holding apparatus having a rod assembly is preferred, however. It is particularly advantageous for a balanced rod assembly to be used on the rear side of the peritoneal dialysis machine or of its machine housing, wherein the front side is free of fastening means so that there is good accessibility to the pan or to the receiving bag received therein.

This arrangement of the holding apparatus facilitates the placing of the receiving bag or bags into the pan from the front, i.e. from the operating side of the peritoneal dialysis machine.

The spacing between the weighing pan and the heating pan in the vertical direction is preferably between 80 cm and 1.2 m, and preferably between 90 cm and 1.1 m.

Provision can furthermore be made that the peritoneal dialysis machine has at least one machine housing and that the fluid control valve or valves, which is/are arranged between the solution bag and the patient, is/are located at the machine housing of the peritoneal dialysis machine.

The at least one drainage valve, which is located between the patient line and the drainage bag, can be located at a machine housing support, with provision preferably being made that the drainage valve is located at a height of 30 cm to 60 cm, preferably at a height of 35 cm to 55 cm, above the floor on which the peritoneal dialysis machine stands. This allows a comfortable operation of the valve by the patient; in this respect, the higher the arrangement, the better. At the same time, the hydrostatic pressure in the system is still sufficiently high to be able to remove the air located in the hose system in a flushing step; in this respect, the lower the arrangement, the better.

Known peritoneal dialysis machines have a multi-point base having a plurality of arms which extend outwardly from a center and at which casters are arranged. Provision is preferably made that the peritoneal dialysis machine is formed with a U-shaped pedestal. It can be of narrow design. It allows an improved sturdiness and stability of the machine and, apart from this, is space-saving. If the limbs of the pedestal are flat, this furthermore allows the arrangement of the pan for the receiving bag close to the floor. The pedestal is preferably designed without casters.

The peritoneal dialysis machine preferably has a spacing between the heating pan as the uppermost point and the pan for the receiving bag as the lower point of <1.2 m, and preferably of <1.1 m. The machine is thus compact and stable. The spacing is preferably between 80 cm and 1.2 m. This difference is required to ensure an error-free inflow and outflow.

To be able to hold the plurality of solution bags securely, the heating pan and/or the weighing pan has/have a base and side walls extending upwardly from the base or laterally elevated fastening plates in a preferred embodiment, with provision preferably being made that one or more of the side walls or of the fastening plates being removable from the base or being pivotable relative to the base e.g. via at least one hinge. This simplifies the placing in and the removal of bags.

Plug-in connections can be provided for the removal and installation of the side walls or of the fastening plates.

The peritoneal dialysis machine in accordance with the invention allows an optimized gravimetric peritoneal dialysis treatment overall.

In a preferred embodiment of the invention, the heating bag and also the weighing bag can be dispensed with. The hose length between the solution bags and the Y piece to the patient connector can furthermore be shortened from 1.5 m to less than 1 m (with a simultaneous connection of a plurality of solution bags).

It is conceivable that the hose set has first line sections which extend from the connectors for the solution bags to a Y piece, wherein a second line section is connected to the Y piece and extends from the Y piece to the connector for the receiving bag or bags or for the one or more lines connected thereto, and wherein a third line section is connected to the Y piece and extends from the Y piece to the connector for the patient line, wherein the first line sections each have a length in the range from 50 cm to 80 cm, preferably in the range from 60 cm to 70 cm, wherein the second line section has a length in the range from 25 cm to 45 cm, preferably in the range from 30 cm to 40 cm, and wherein the third line section has a length in the range from 1.9 m to 2.2 m, preferably in the range from 2.0 m to 2.1 m. Instead of a Y piece, any other connector is also conceivable and is covered by the invention.

A further benefit of the hose set is that a breakable connector is used such as is known from EP 1 351 726, to which reference is made in this respect. The emptied solution bags can thus be separated from the hose set by breaking the connector after the treatment and can be connected to a new hose or hose set. These bags then serve as outflow bags, i.e. as drainage bags.

The present invention furthermore relates to the use of a hose set in a peritoneal dialysis machine in accordance with the invention. The hose set is not connected to a heating bag and/or not to a weighing bag from which the consumed dialyzate is transferred into a waste bag. The hose set can be configured in accordance with the further above-named features.

BRIEF DESCRIPTION OF THE DRAWINGS

Further advantages and particulars of the invention will be explained in more detail with reference to an embodiment shown in the drawing.

There are shown.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
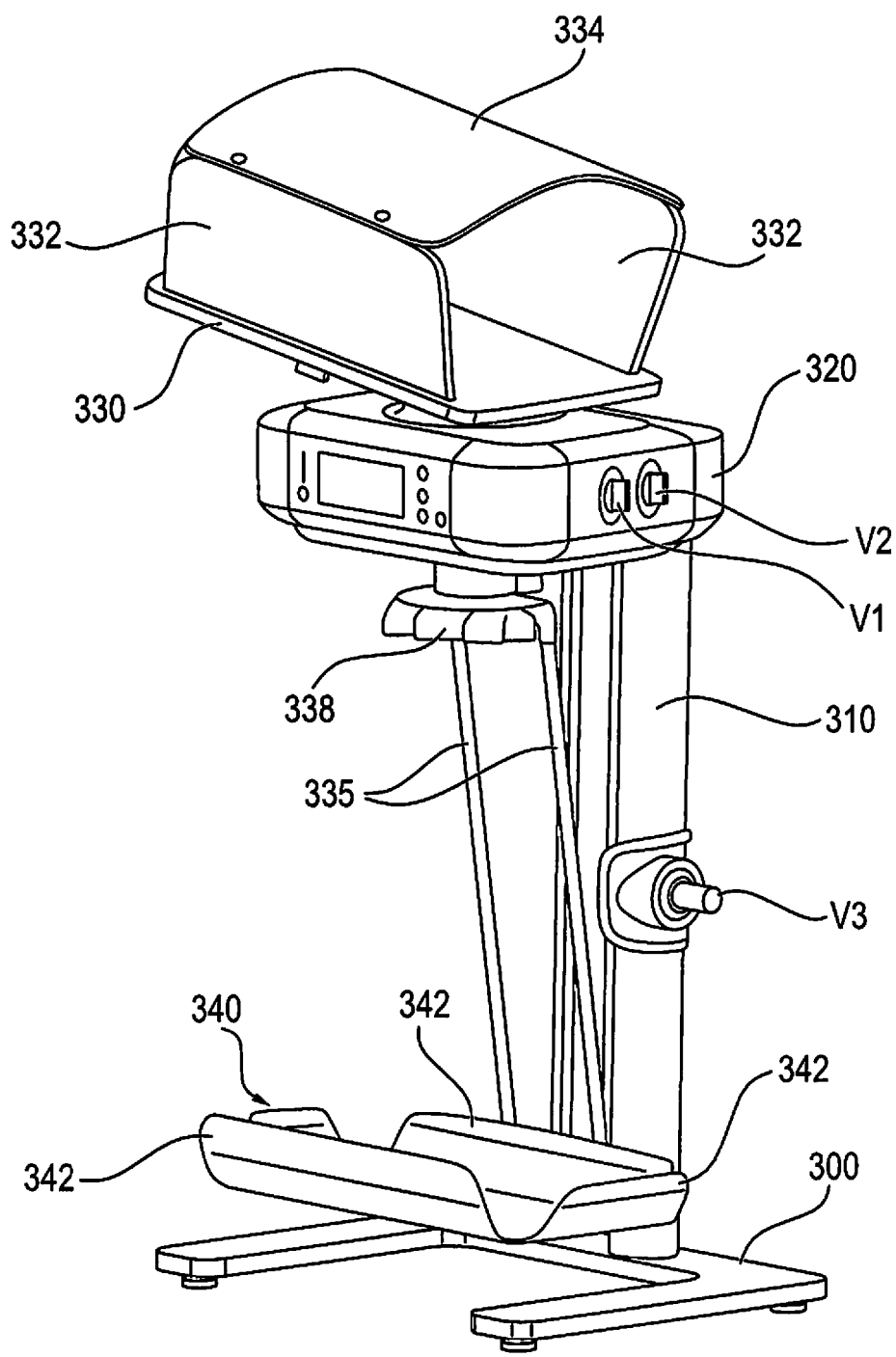
FIG. 1: a perspective view of a peritoneal dialysis machine in accordance with the invention.

FIG. 1 shows a peritoneal dialysis machine in accordance with the present invention in a perspective view.

The peritoneal dialysis machine has a U-shaped pedestal 300 from which a machine housing support 310 extends vertically upwardly. The machine housing 320 is located at its upper end. The electronics required for operating the machine, such as control and regulation units, and the operating and/or display units, are located in the machine housing 320.

The heating pan 330 which serves the reception of solution bags containing fresh dialyzate to be supplied to the patient is arranged directly above the machine housing 320, directly connected thereto.

A rod assembly 335 at which the weighing pan 340 is arranged is located at the bottom at the machine housing 320 or at the weighing cell 338. The weighing pan 340 serves the reception of one or more receiving bags into which the used dialyzate coming from the patient moves.

As can be seen from FIG. 1, the weighing pan 340 is located directly above the floor on which the pedestal 300 of the peritoneal dialysis machine stands. It can furthermore be seen from FIG. 1 that the pedestal has a flat profile so that the weighing pan 340 can be arranged far to the bottom.

The spacing between the base of the weighing pan 340 and the floor amounts, for example, to a few cm, e.g. 5 cm to 10 cm, and preferably 7.5 cm to 8.5 cm.

The spacing between the base of the heating pan 330 and the base of the weighing pan 340 is preferably between 80 cm and 1.2 m.

The fluid control to and from the patient takes place via valves, wherein the valve or valves for the fluid connection between the solution bag or bags, which are located in the heating pan 330, and the patient are arranged at the machine housing 320. These valves are marked by the reference symbols V1, V2 in FIG. 1. The drainage valve V3, which is arranged between the patient and the receiving bag for consumed dialyzate, is located at the machine housing support 310. It is arranged at a height of approximately 40 cm to 50 cm, and preferably of 45 cm, above the floor. This allows a comfortable operation by the patient.

As can be seen from FIG. 1, the rod assembly 335 extends from the rear side of the weighing pan 340 upwardly to the lower side of the machine housing 320. A good accessibility from the front side to the weighing pan 340 is thus present.

The rod assembly 335 is arranged at a weighing cell 338 which is located at or in the machine housing 320.

Both the heating pan 330 and the weighing pan 340 have a support surface for the bag or bags which represents the base. Side walls 332 and 342 extend upwardly starting from the base. They have the object of holding the respective received bags securely in the pan. This is in particular of importance when a plurality of bags are received in the heating pan 330 and in the weighing pan 340.

The side walls 332 and 342 can be fastened by a plug-in connection or can be pivotable relative to the support surface so that the bags can be placed in and removed easily.

The heating pan 330 is furthermore provided with an upper cover 334 which has the object of keeping the heat, where possible, in the region of the solution bags which are located in the heating pan 330.

Figure 2:
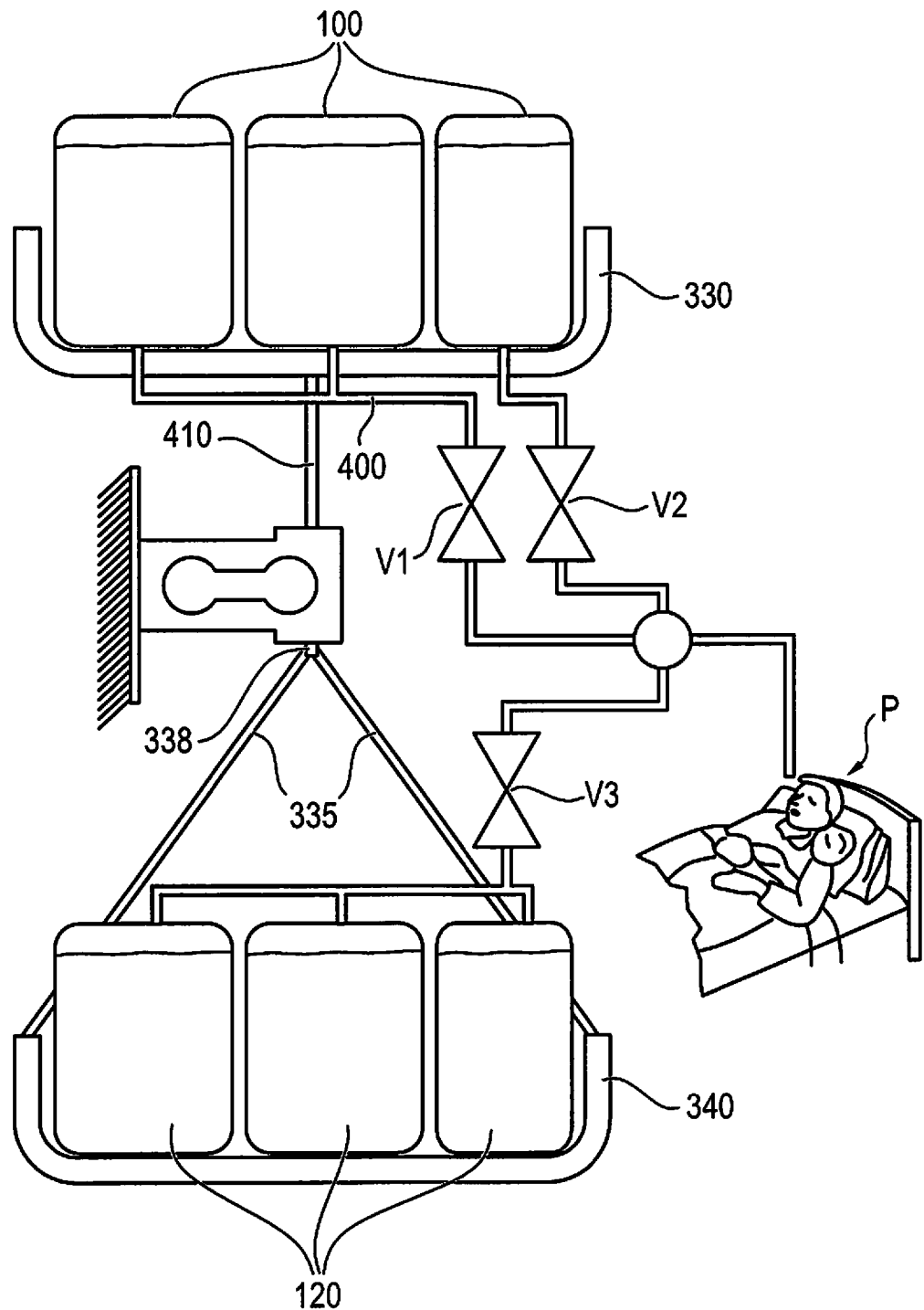
FIG. 2: a schematic view of a peritoneal dialysis machine in accordance with the invention.

FIG. 2 shows the peritoneal dialysis machine in accordance with FIG. 1 in a schematic view. In the embodiment shown here, three solution bags 110 are located in the heating pan 330 and each contain dialyzate which is to be supplied to the patient P. The two solution bags shown on the left are connected to one another by a Y piece 400. The valve V1 is located downstream of the Y piece 400. The solution bag shown on the right is likewise separated from the patient P by a valve V2.

The respective dialyzate is supplied to the patient P by opening the valves V1, V2.

The heating pan 330 is fixed at the top on the machine housing 320 by a rod assembly 410. It can be connected to a weighing device such that the weight in the solution bags 100 can be measured in the heating pan 330.

The weighing pan 340 in which a plurality of receiving bags 120 are arranged for receiving the consumed dialyzate coming from the patient is located beneath the machine housing 320. The number and the volume of the receiving bags 120 correspond to those of the solution bags 100.

The valve V3 is located between the patient and the receiving bags 120. If it is opened, the dialyzate moves from the patient into the receiving bag. The consumed dialyzate is collected in the receiving bags 120. No conducting onward to one or more other bags takes place.

Figure 12:
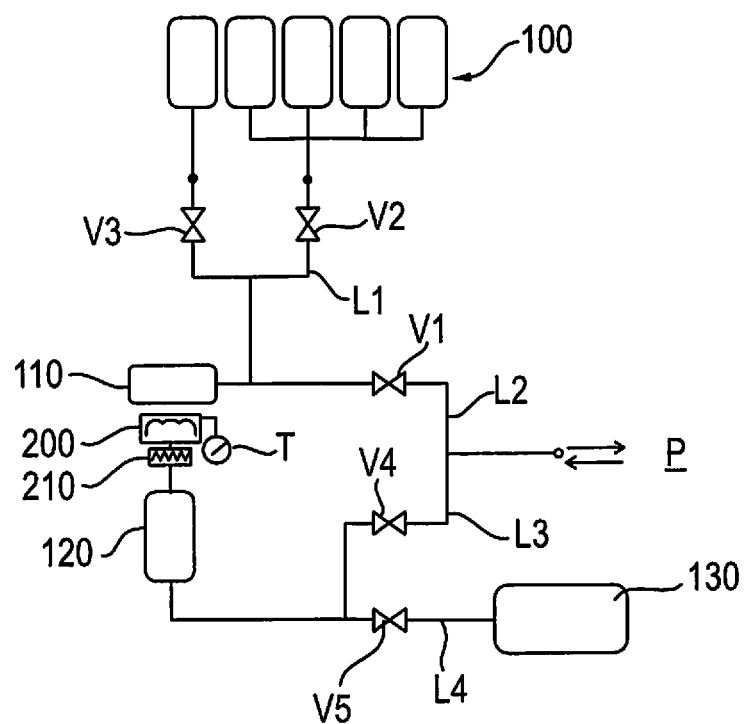
FIG. 12: a schematic view of the components of a peritoneal dialysis machine in accordance with the prior art.

A comparison of the arrangement in accordance with FIGS. 1 and 12 shows that a separate heating bag can be dispensed with in the arrangement in accordance with the invention since the solution bags themselves are received in the heating pan. Furthermore, a weighing bag only serving for weighing can be dispensed with in the arrangement in accordance with the invention since the receiving bags themselves are weighed.

Not only a dispensing with of the heating and weighing bags is thereby possible, but also a dispensing with of the valves V1 and V5.

This brings about the advantage of a correspondingly simplified hose set. Due to the smaller height of the total machine, the hoses used can be configured shorter with respect to known arrangements.

As stated above, a further simplification can be achieved in that the hose set is provided with at least one breakable connector such as is known from EP 1 351 726. The emptied solution bags 100 are separated after the treatment by breaking the connector and are connected to a new hose set. These bags can then serve as drainage bags or as receiving bags in the new hose set.

Further advantages comprise no last bag with a diluted solution having to be provided and shorter treatment times being able to be achieved since the repeated filling of a heating bag and of a weighing bag is omitted.

Due to the fact that the drainage valve is arranged relatively far to the bottom, the patient can likewise be at a lower level than with known devices.

The peritoneal dialysis machine preferably has a total height of <1.1 m. Its width and depth are preferably in the range from <1 m×<1 m, and preferably at <80 cm×<80 cm. The pedestal, for example, has a width and a depth of <1 m, and of preferably <80 cm, and is preferably without casters.

It is pointed out that the term "bag" is representative for any desired container which is suitable for receiving solutions. It can have fixed walls or flexible walls.

The term pan is furthermore not restricted to a pan in a narrower sense, but rather covers any desired receiver for the bag or bags.

The hose set comprises lines and can be in one part or in multiple parts.

Figure 3:
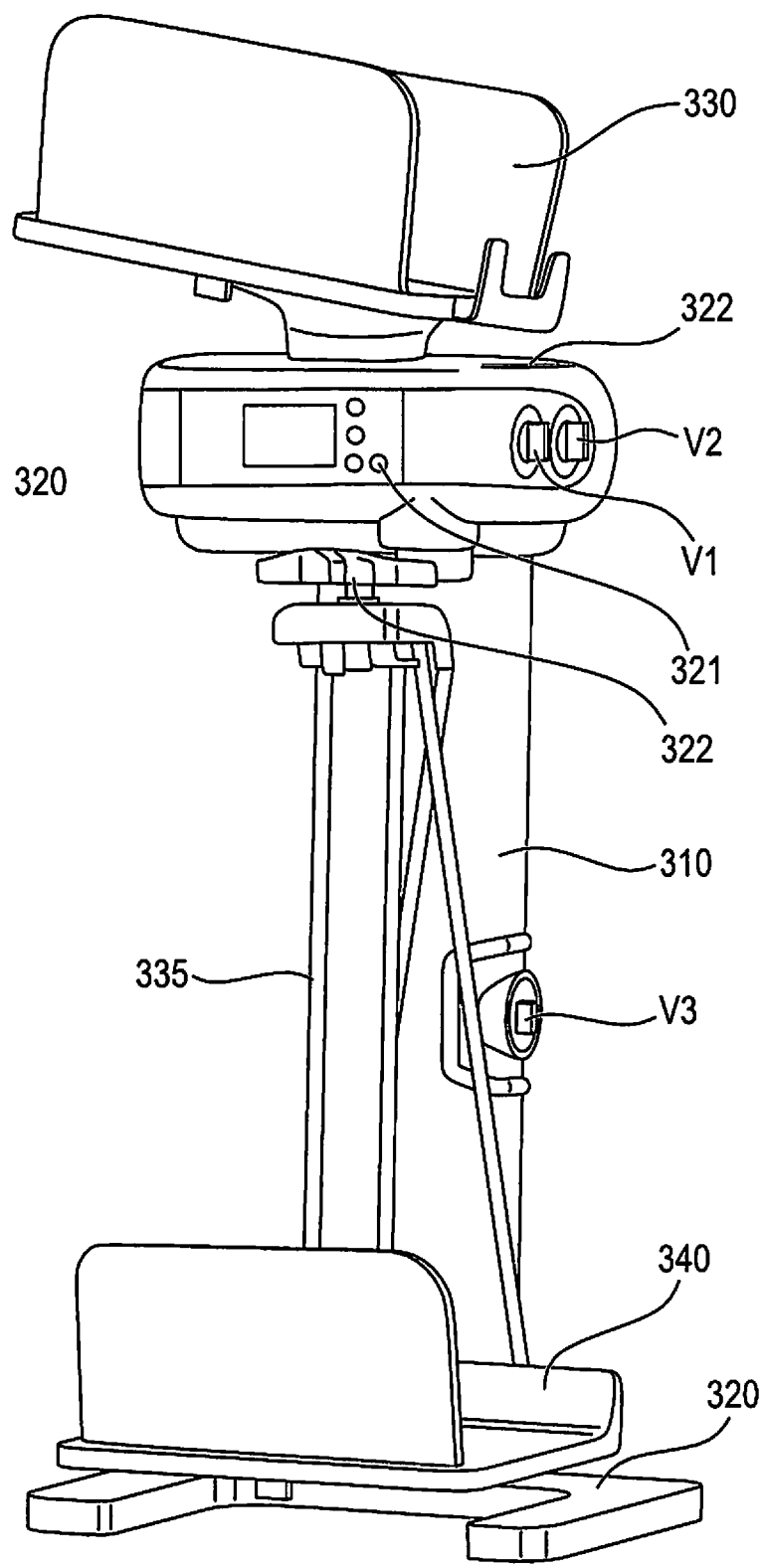
FIG. 3: a further perspective view of a peritoneal dialysis machine in accordance with the invention.
Figure 4:
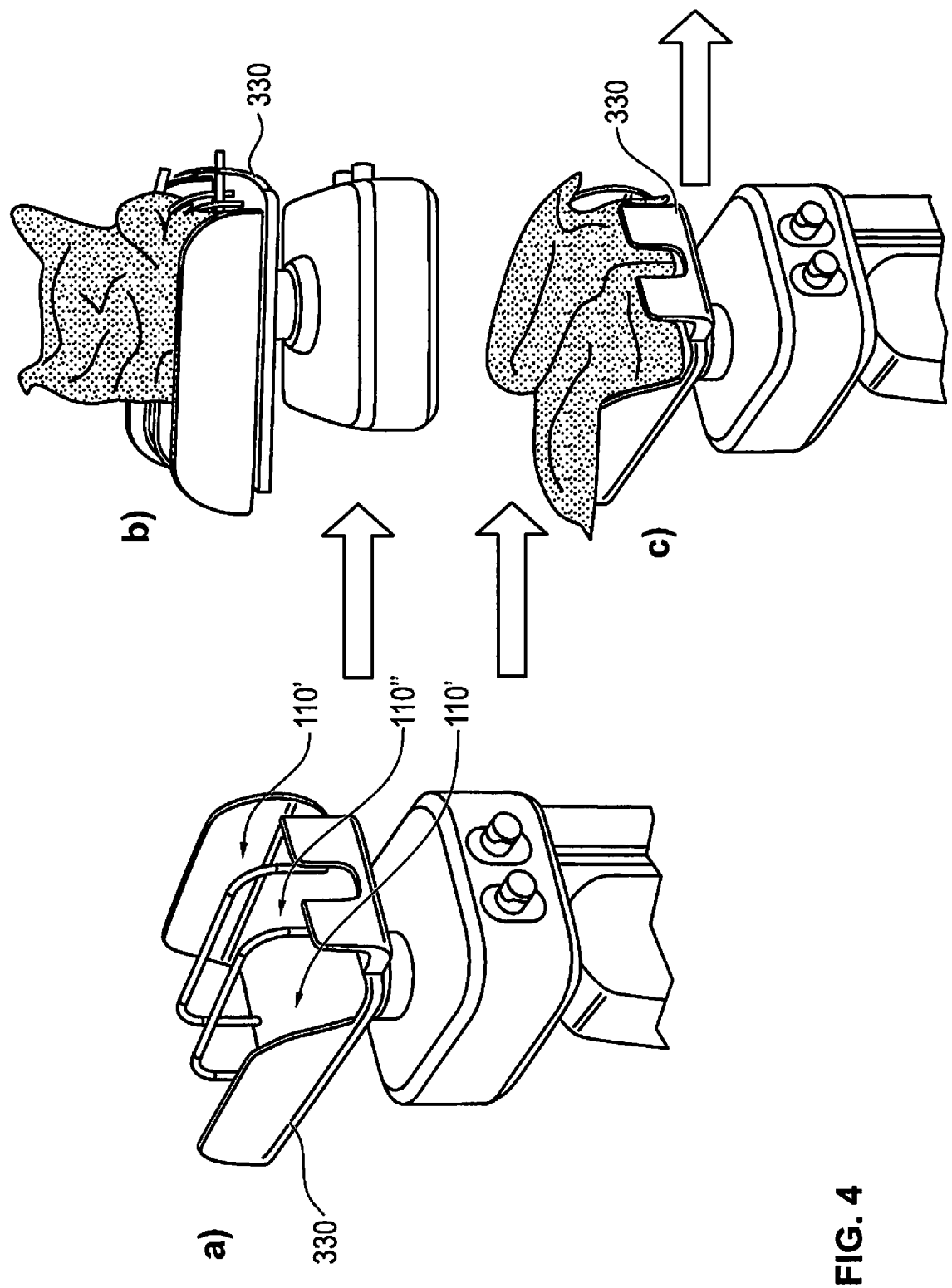
FIG. 4: views of a heating pan with and without solution bags.

FIG. 3 shows a further perspective view of a peritoneal dialysis machine in accordance with the invention.

In FIGS. 3 to 11, the same parts or parts of the same function are provided with the same reference numerals as in FIGS. 1 and 2.

The heating pan 330 forms the topmost point of the machine. The machine housing 320 is located beneath the heating pan. An introduction slit 322, e.g. for a patient card, is located in said machine housing.

Reference numeral 321 characterizes the operating panel having one or more keys for operating the machine and having a screen which can be designed as a conventional display screen or as a touch screen.

Reference symbol V1 indicates the valve which is arranged at the machine housing 320 and forms a fluid control valve which controls the inflow of the solution from the solution bags (except for the last bag) toward the patient.

Reference symbol V2 indicates the valve for the last bag, that is for the last dispensed solution bag.

As can be seen from FIG. 3, both valves are arranged at the machine housing 320.

A so-called organizer which serves the reception of connectors of the hose set with further lines and the patient connector is marked by reference numeral 322.

Reference numeral 310 represents the machine housing support at whose upper end the machine housing 320 is located and at whose lower end the machine stand 320 is located.

The drainage valve V3 is located at the machine housing support 310 and cooperates with the line section which extends from the patient to the receiving bag or bags and with the line section which extends (for flushing purposes) from the solution bag or bags to the receiving bag or bags.

Reference numeral 335 marks a rod assembly which is connected at its upper end to a weighing cell which is arranged in the housing 320 and which holds the weighing pan 340 at its lower end. One or more receiving bags for receiving the consumed dialyzate are located in said weighing pan.

FIG. 4a) shows, in a perspective view, the heating pan 330 which is divided by brackets or other separation elements into different regions 110', 110" and 110'. The heating pan can also be designed without separation elements which separate its receiving region into a plurality of part regions.

Solution bags are located in the regions 110' and the so-called last bag is preferably located in the region 110".

FIG. 4b) shows the reception of a single-chamber bag in the heating pan 330 and FIG. 4c) shows the reception of a double-chamber bag in the heating pan 330.

Figure 5:
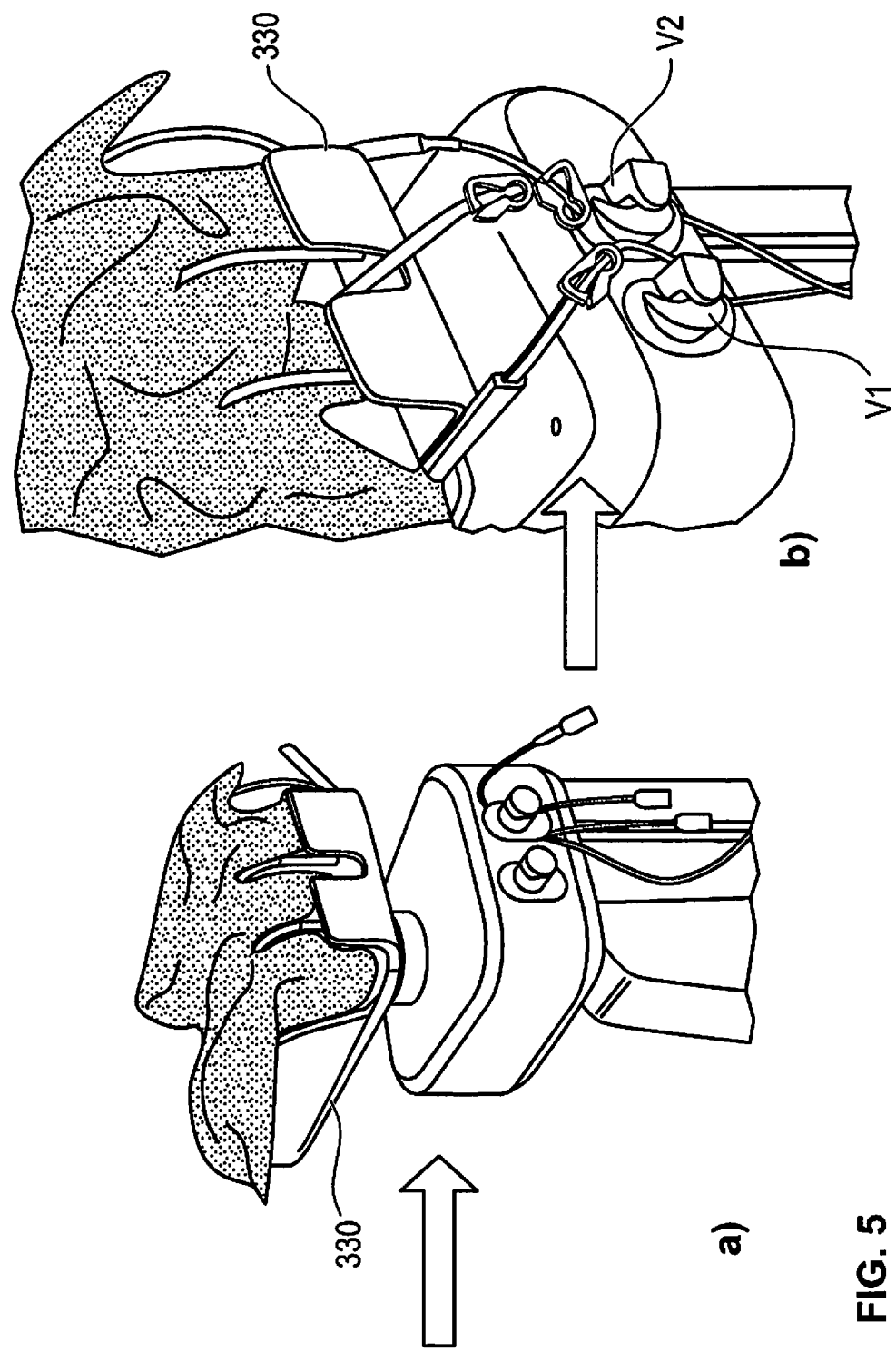
FIG. 5: views of a heating pan with solution bags arranged next to one another.

The state results from a particularly preferred embodiment in accordance with FIG. 5 in which the solution bags are received in the heating pan 330 and the hose set is already received in the valves V1 and V2.

The solution bags 100, which do not represent the last bag, are connected to one another via a Y piece.

The line section extending downstream of this Y piece is located in the valve V1 at the machine side. The line which is connected to the last bag is located in the valve V2 arranged at the machine side.

Figure 6:
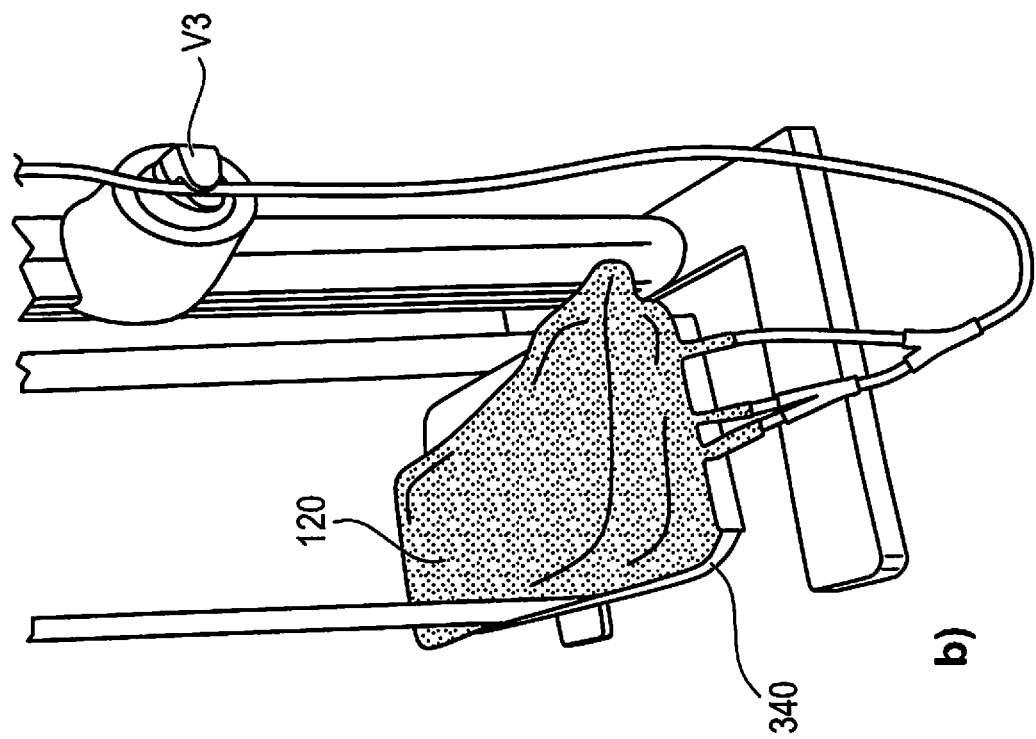
FIG. 6: a view of the drainage valve and of the weighing pan.
Figure 6:
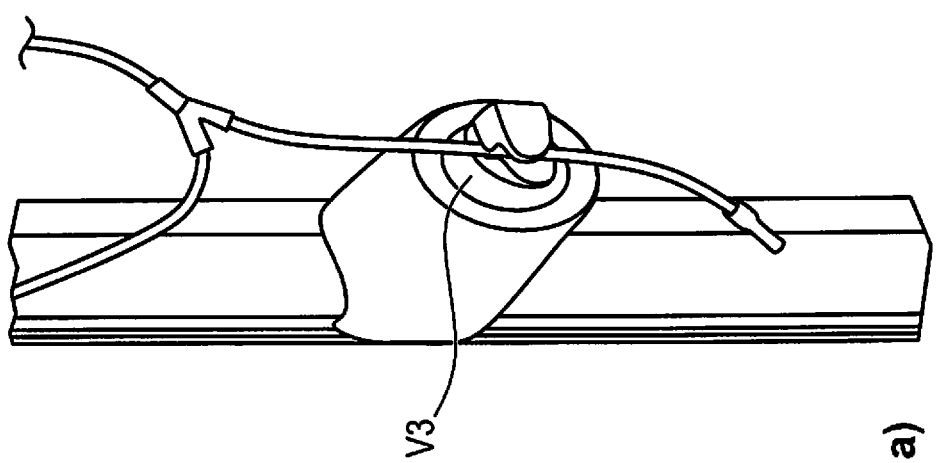

FIG. 6 shows the drainage valve V3 in an enlarged view in the view a.

This valve is located at the machine housing support 30 and accepts the line section of the hose set which leads from the patient connector and from the solution bags to the receiving bag or to a line which is connected to the receiving bags 120. A plurality of receiving bags 120 for receiving the consumed dialyzate are preferably located in the weighing pan 340 shown in FIG. 6b).

Figure 7:
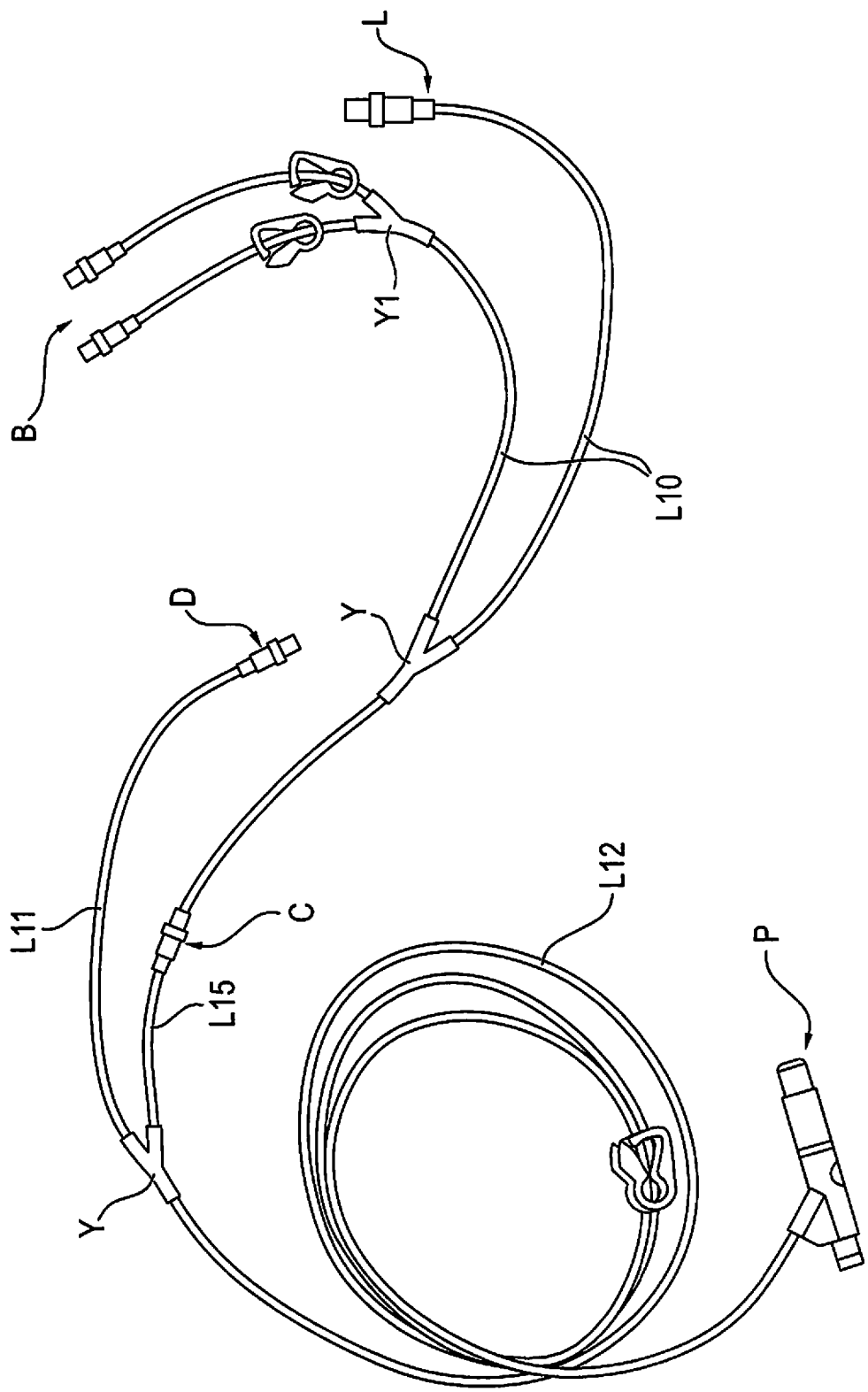
FIGS. 7, 8: a view of the hose set with and without connector lines for the receiving bags.
Figure 8:
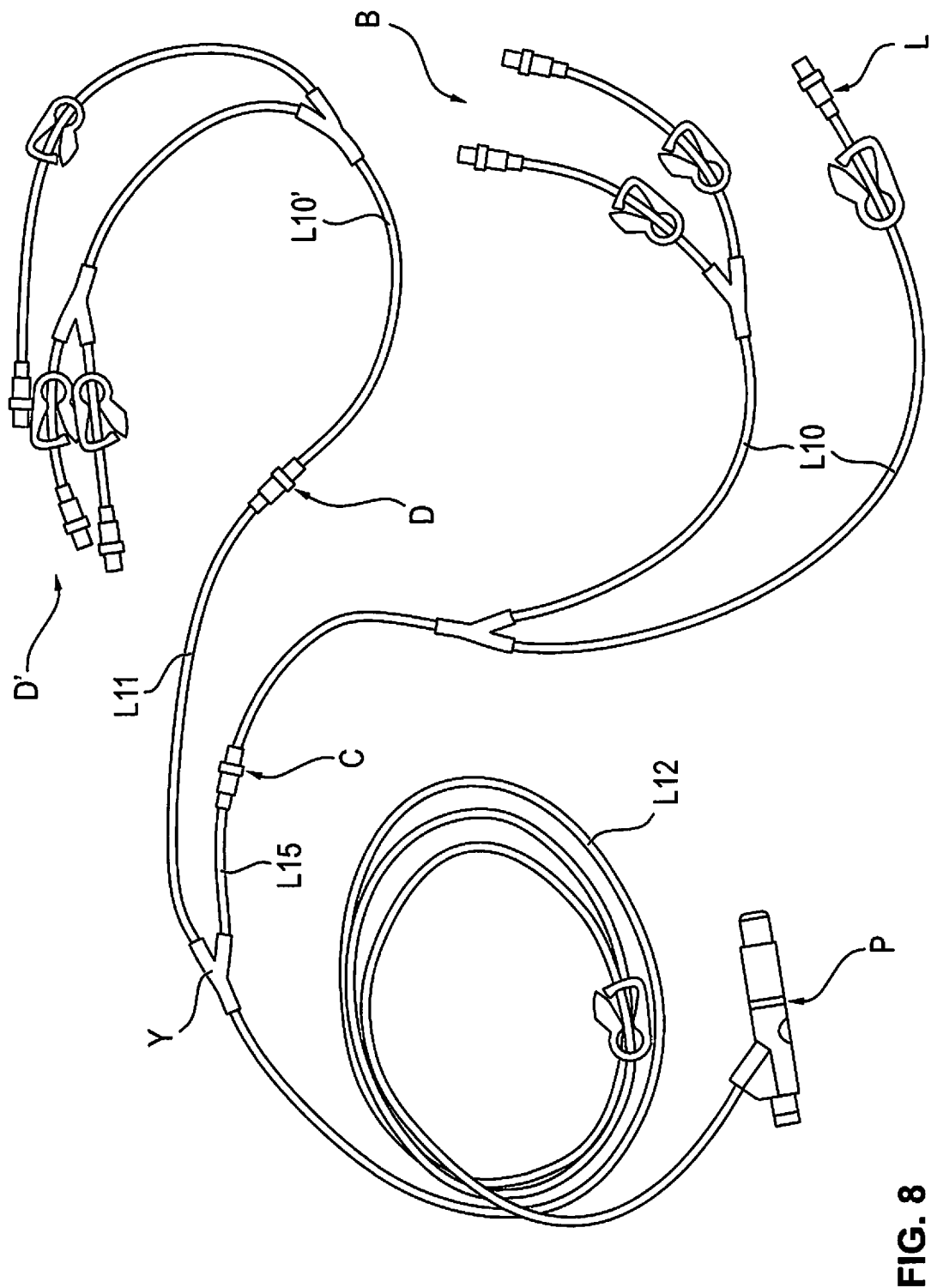

FIG. 7 and FIG. 8 show hose sets which are used in a peritoneal dialysis machine in accordance with the present invention in a particularly preferred embodiment.

In this respect, the first line sections each have a length in the range from 50 cm to 80 cm, preferably in the range from 60 cm to 70 cm, the second line section has a length in the range from 25 cm to 45 cm, preferably in the range from 30 cm to 40 cm, and the third line section has a length in the range from 1.9 m to 2.2 m, preferably in the range from 2.0 m to 2.1 m.

The hose set comprises the patient connector P and a line section L12 leading therefrom to a Y piece "Y". The line section L12 preferably has a length in the range from 1.9 m to 2.2 m, preferably in the range from 2.0 m to 2.1 m.

A line L11 branches off from the Y piece whose end is formed by the connector D. The receiving bag or a line which is connected to one or more receiving bags is connected to this connector. The line section L11 preferably has a length in the range from 25 cm to 45 cm, preferably in the range from 30 cm to 40 cm.

The line piece L15 likewise branches off from the Y piece and ends at the separable connector C which is preferably a breakable Luer lock connector. The line section L15 preferably has a length in the range from 15 cm to 25 cm.

The line section L10 extends from this connector C to the connectors B for the solution bags, which do not represent the last bag, and to the connector L which is connected to the last bag. The line sections from the Y piece "Y" up to the connectors B for the solution bags preferably have a length in the range from 50 cm to 80 cm, and preferably in the range from 60 cm to 70 cm. The same applies accordingly in a preferred embodiment for the line section from the Y piece "Y" up to the connector L for the last bag. It is, however, preferably 3 cm to 7 cm longer.

As can be seen from FIG. 7, the lines which are connected to the connectors B are connected via a Y piece Y1. The common line opening from this Y piece is connected via the further Y piece Y2 to the line which leads to the last bag.

The length of the line section between the connector C and the Y piece "Y2" is preferably in the range from 3 cm to 7 cm, the length of the line section between the Y piece "Y2" and the Y piece "Y1" is preferably in the range from 15 cm to 25 cm, and the length of the line section between the Y piece "Y2" and the connector L is preferably in the range between 40 cm and 50 cm, and the length of the line section between the Y piece "Y1" and the connectors B is preferably in the range between 15 cm and 25 cm.

An arrangement can be seen from FIG. 8 which substantially corresponds to that explained with respect to FIG. 7 so that reference is made accordingly. In the arrangement in accordance with FIG. 8, the line system L10 is separated at the connector C and is connected to a new hose set. The previous lines L10 of the used hose set are marked in FIG. 8 by the reference symbol L10. They are connected to the connector D of a new hose set and their end regions are connected to receiving bags which are received in the weighing pan 340.

Respective line sections L10, which are connected to the solution bags 100, are thus separated after the treatment or after the inflow into the patient at the point C and are connected to the connector D of a new hose set.

Figure 9:
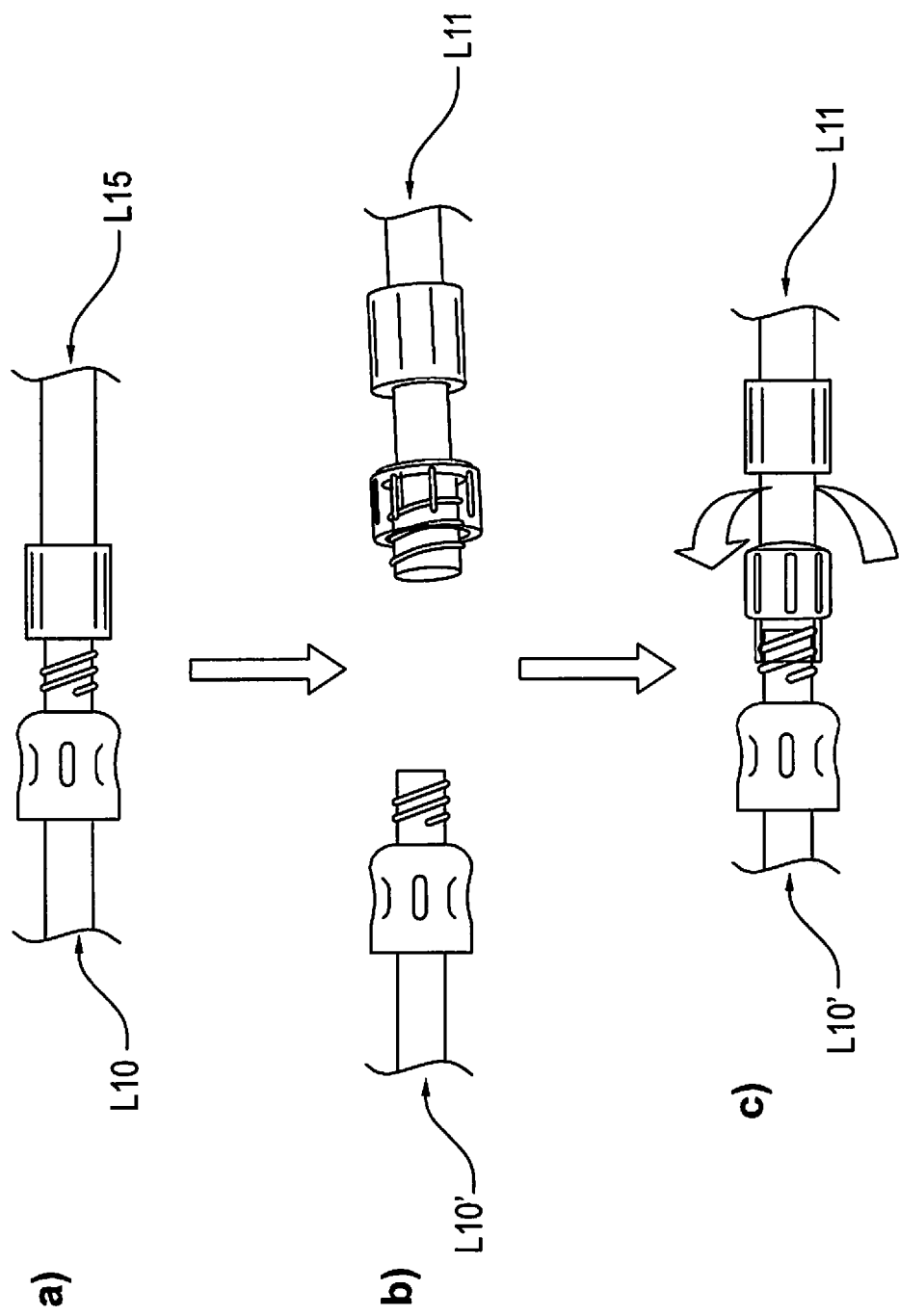
FIG. 9: a representation of the steps for separating the lines of the solution bags from a used hose set and for connecting the connector lines for the receiving bags to a new hose set.

This procedure also results from FIG. 9. FIG. 9*a* shows by the reference symbol L10 the line which leads to the emptied solution bags 100 and by the reference numeral L15 the line of the hose set connected to this line via the connector. This line connection is separated and the line system L10' in accordance with FIG. 8 is now connected to a new hose set which is marked by reference symbol L11 in FIG. 9*b*. The process of the connection can be seen from FIG. 9*c*.

Figure 10:
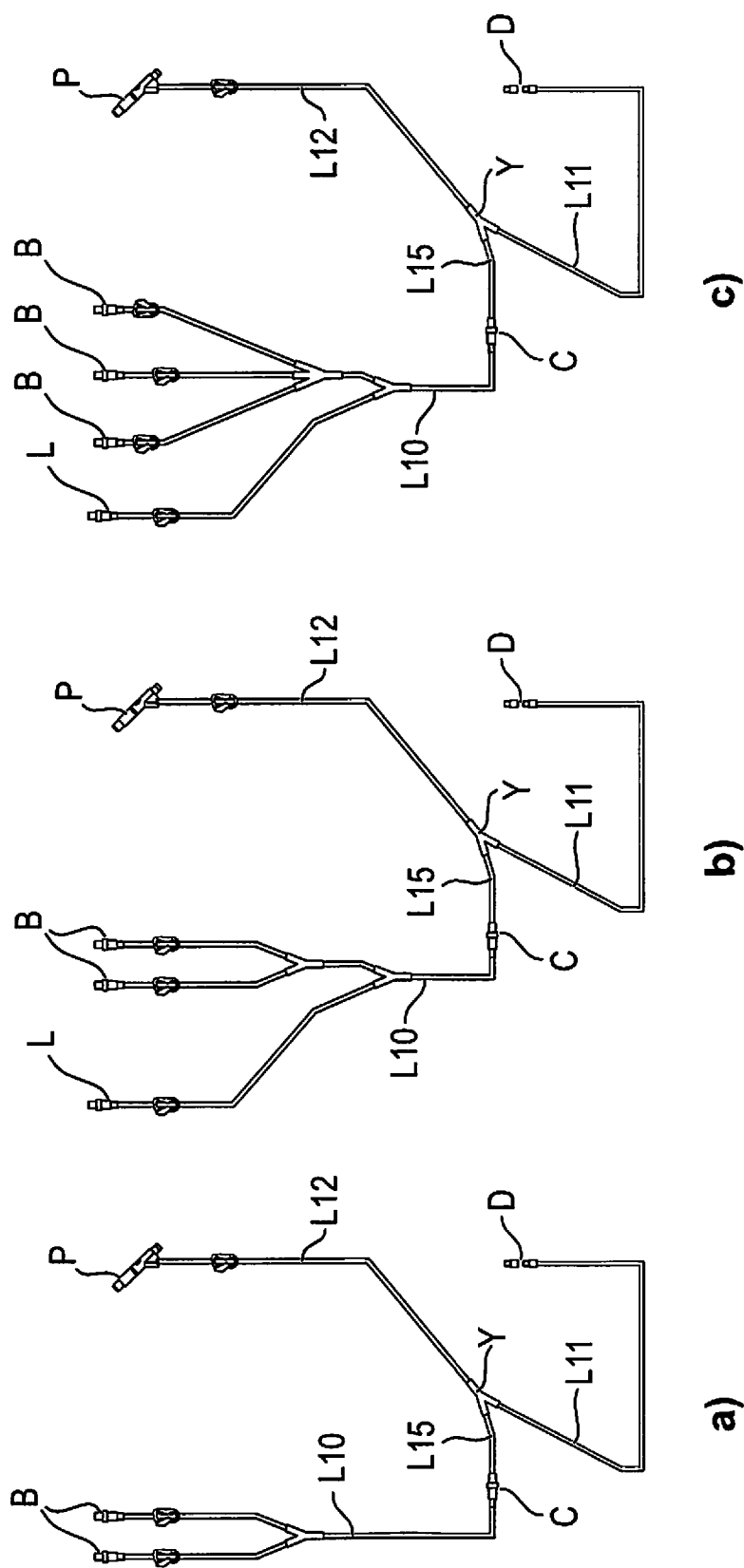
FIG. 10: different embodiments of hose sets.

FIG. 10 shows different embodiments of hose sets in accordance with the invention, wherein the reference numerals which are the same refer to elements which are the same or have the same function.

FIG. 10*a* shows a hose set without a line for the last bag, but having two line connectors or connectors B for solution bags.

FIG. 10*b*) shows an arrangement in which a last bag is additionally used which is connected via the connector L and FIG. 10*c*) shows an arrangement having three lines or connectors B for solution bags and a connector L for the last bag.

Figure 11:
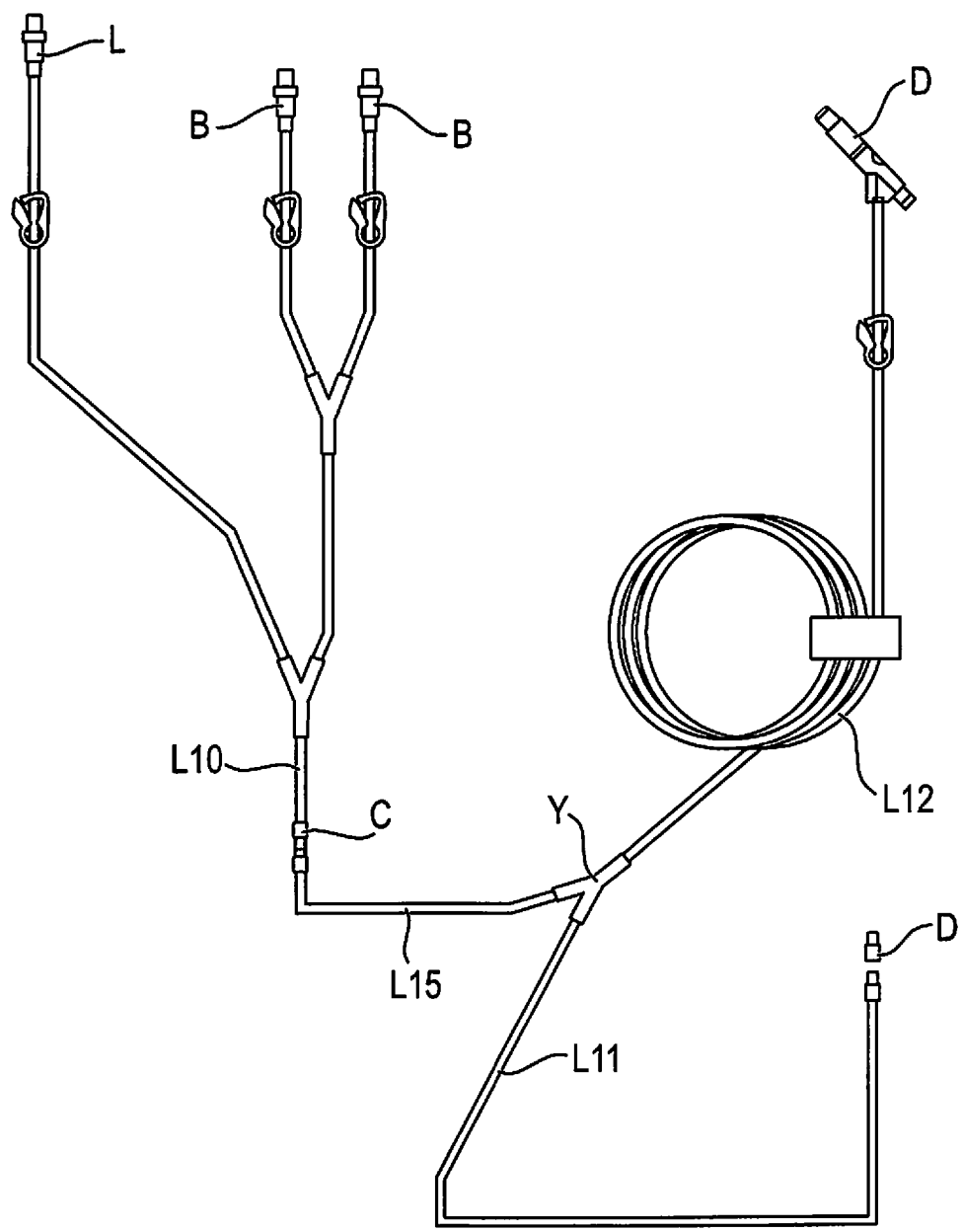
FIG. 11: a hose set having two lines for solution bags, having a connector line for the "last bag", having a line for the connection to the patient line and having a line for the connection to a receiving bag or having one or more lines leading to the receiving bags.

The arrangement in accordance with FIG. 10*b*) is shown again in FIG. 11.

The releasable connection point C at which the line L10 is separated from the line L15 after the flowing of the solutions into the patient also results from this Figure. This line L10 is then attached as the line L10' to the connector D of a new hose set and is connected to receiving bags.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A peritoneal dialysis machine comprising at least one machine housing supported on a machine housing stand, at least one weighing cell arranged in or at the machine housing, at least one heating pan, a plurality of solution bags arranged in said heating pan with no heating bag being present into which liquid draining from the solution bags runs, at least one hose set which is connected to the solution bags, a weighing device having at least one weighing pan, and at least one holding apparatus connecting said weighing pan to said weighing cell, said at least one holding apparatus including at least one rod assembly which is located at a rear side of the machine housing remote from a front side of said machine housing, wherein-the weighing pan is arranged at a height of <20 cm above a floor on which the peritoneal dialysis machine stands, and wherein a spacing between the weighing pan and the heating pan in the vertical direction is in a range between 80 cm and 1.2 m.

2. A peritoneal dialysis machine comprising a machine housing supported on a machine housing stand, at least one weighing cell arranged in or at the machine housing, at least one holding apparatus, at least one weighing device having at least one weighing pan into which at least one receiving bag is arranged for receiving draining dialyzate, at least one heating pan, and at least one hose set which is connected to the at least one receiving bag, said at least one receiving bag not being in fluid communication with a waste bag in which the drained dialyzate is collected, but rather said at least one receiving bag itself forming the waste bag, said weighing pan being connected via said at least one holding apparatus to said at least one weighing cell, and said at least one holding apparatus including at least one rod assembly which is located at a rear side of the machine housing remote from a front side of said machine housing, wherein-the weighing pan is arranged at a height of <20 cm above a floor on which the peritoneal dialysis machine stands, and wherein a spacing between the weighing pan and the heating pan in the vertical direction is in a range between 80 cm and 1.2 m.

3. The peritoneal dialysis machine in accordance with claim 2, wherein the peritoneal dialysis machine further comprises a plurality of solution bags and at least one hose set which is connected to the solution bags, the plurality of solution bags being arranged in the heating pan; and no heating bag being present into which liquid draining from the solution bags runs.

4. The peritoneal dialysis machine in accordance with claim 1, wherein the peritoneal dialysis machine does not have an IV pole to which solution bags can be fastened.

5. The peritoneal dialysis machine in accordance with claim 1, wherein the peritoneal dialysis machine has at least one IV pole to which one or more solution bags are fastened.

6. The peritoneal dialysis machine in accordance with claim 1, wherein the heating pan is arranged above the machine housing and is directly connected to the machine housing.

7. The peritoneal dialysis machine in accordance with claim 1, wherein the solution bags are arranged above one another and/or next to one another in the heating pan.

8. The peritoneal dialysis machine in accordance with claim 1, wherein said peritoneal dialysis machine is a gravimetrically operating peritoneal dialysis machine that has no pumps for the conveying of solutions.

9. The peritoneal dialysis machine in accordance with claim 1, wherein the hose set is configured such that it is simultaneously connected to at least two solution bags of different contents such that a mixed solution can be prepared.

10. The peritoneal dialysis machine in accordance with claim 1, wherein the hose set is arranged such that the hose set only cooperates with exactly one fluid control valve of the peritoneal dialysis machine between a connector or connectors for at least one of said solution bags and the end of the hose set by which it is connected to the patient line.

11. The peritoneal dialysis machine in accordance with claim 2, wherein the hose set is arranged such that the hose set only cooperates with exactly one drainage control valve of the peritoneal dialysis machine between the end of the hose set by which it is connected to the patient line and a connector for the receiving bag.

12. The peritoneal dialysis machine in accordance with claim 10, wherein at least one fluid control valve is located at the machine housing of the peritoneal dialysis machine.

13. The peritoneal dialysis machine in accordance with claim 1, wherein the peritoneal dialysis machine is configured with a U-shaped pedestal; and the peritoneal dialysis machine has a total height of <1.2 m.

14. The peritoneal dialysis machine in accordance with claim 1, wherein at least one of the heating pan and the weighing pan has a base and side walls extending upwardly from the base, and wherein one or more of the side walls can be removed from the base.

15. The peritoneal dialysis machine in accordance with claim 1, wherein the hose set is configured as disposable;

and/or in that the hose set has at least two connectors for the solution bags and a connector for connection to the patient line.

16. The peritoneal dialysis machine in accordance with claim 1, wherein the hose set has a total length of 3 m to 4.5 m.

17. The peritoneal dialysis machine in accordance with claim 1, wherein the hose set has first line sections which extend from connectors for the solution bags to a branching piece, wherein a second line section is connected to the branching piece and extends from the branching piece to the connector for a receiving bag or for one or more lines connected thereto, and wherein a third line section is connected to the branching piece and extends from the branching piece to a connector for the patient line, wherein the first line sections each have a length in the range from 50 cm to 80 cm, wherein the second line section has a length in the range from 25 cm to 45 cm, and wherein the third line section has a length in the range from 1.9 m to 2.2 m.

18. The peritoneal dialysis machine in accordance with claim 1, wherein the hose set is not connected to a heating bag and wherein the hose set is not connected to a weighing bag from which consumed dialyzate runs into a waste bag.

19. The peritoneal dialysis machine in accordance with claim 2, wherein at least one drainage control valve is located at at least one machine housing support and is positioned between an end of the hose set connected to the patient line and a connector for the receiving bag, said drainage control valve being located at a height of 30 cm to 60 cm above a floor on which the peritoneal dialysis machine stands.

20. The peritoneal dialysis machine in accordance with claim 1, wherein the weighing pan has a base and side walls extending upwardly from the base, and wherein one or more of the side walls can be pivoted relative to the base.

\* \* \* \* \*